United States Patent [19]
Ito et al.

[11] Patent Number: 6,022,867
[45] Date of Patent: Feb. 8, 2000

[54] METHOD OF ADMINISTERING VITAMIN E TO ANIMALS AND COMPOSITIONS CONTAINING TOCOPHERYL PHOSPHATES AND SALTS THEREOF FOR ANIMALS

[75] Inventors: Shinobu Ito; Eiji Ogata, both of Tokyo, Japan

[73] Assignee: Showa Denko Kabushiki Kaisha, Tokyo, Japan

[21] Appl. No.: 08/980,371

[22] Filed: Nov. 28, 1997

Related U.S. Application Data

[60] Provisional application No. 60/047,102, May 19, 1997.

[30] Foreign Application Priority Data

Nov. 27, 1996 [JP] Japan ..................... 8-332931

[51] Int. Cl.⁷ ........................ A61K 31/665; A61K 31/355
[52] U.S. Cl. ............................... 514/100; 514/458
[58] Field of Search ...................... 514/100, 458

[56] References Cited

U.S. PATENT DOCUMENTS

| | | |
|---|---|---|
| 5,114,957 | 5/1992 | Hendler et al. . |
| 5,387,579 | 2/1995 | Meybeck et al. ................. 514/100 |

FOREIGN PATENT DOCUMENTS

| | | |
|---|---|---|
| 10646378 | 4/1995 | European Pat. Off. . |
| 10798305 | 10/1997 | European Pat. Off. . |
| 59-044375 | 3/1984 | Japan . |
| 3005426 | 1/1991 | Japan . |
| 918399 | 10/1961 | United Kingdom . |
| WO9315731 | 8/1993 | WIPO . |

OTHER PUBLICATIONS

Gilbert, John J.. "Effect of the non–tocopherol component of the diet on polmorphism, sexuality, . . . A splanchna sieboldi." *Archiv Fur Hydrobiologie*, 80, No. 3, (1977), 377–383.

Caplus Abstract No. 103:54318, Zakharova et al. Khim.–Farm. Zh. 19(1), 75–7, 1985.

*Primary Examiner*—Raymond Henley, Jr.
*Attorney, Agent, or Firm*—Sughrue, Mion, Zinn Macpeak & Seas, PLLC

[57] ABSTRACT

A vitamin E source composition for administration to animals, which comprises a tocopheryl phosphate, a salt thereof or a composition containing a tocopheryl phosphate or a salt thereof. Also, disclosed is a method of supplying vitamin E to animals which comprises administering to animals the above vitamin E source composition. The tocopheryl phosphoric acid and a salt thereof can be formed into a composition and also can contain an antioxidant or the like.

10 Claims, No Drawings

METHOD OF ADMINISTERING VITAMIN E TO ANIMALS AND COMPOSITIONS CONTAINING TOCOPHERYL PHOSPHATES AND SALTS THEREOF FOR ANIMALS

CROSS REFERENCE TO RELATED APPLICATIONS

This application is an application filed under 35 U.S.C. §111(a) claiming benefit pursuant to 35 U.S.C. §119(e)(1) of the filing date of the Provisional Application 60/047,102, filed May 19, 1997, pursuant to 35 U.S.C. §111(b).

BACKGROUND OF THE INVENTION

1. Field of the Invention

The present invention relates to a tocopheryl phosphate, a salt thereof and a composition containing the tocopheryl phosphate or a salt thereof as a source of vitamin E for administration to animals, and to a method of supplying vitamin E to animals which comprises administering to animals the tocopheryl phosphate, a salt thereof or the composition containing the tocopheryl phosphate or a salt thereof. More specifically, the present invention relates to a tocopheryl phosphate, a salt thereof and a composition containing the tocopheryl phosphate or a salt thereof, capable of effectively supplying a source of vitamin E which has great effects on the prevention of aging of animals, the treatment or prevention of diseases, stress relief, increased hatchability, improved egg quality, the treatment or prevention of propagation disorder or mastitis, or reduction in the number of somatic cells in milk. The present invention also relates to a method of administering the tocopheryl phosphate, a salt thereof or a composition containing the tocopheryl phosphate or a salt thereof to animals.

2. Description of the Related Art

Vitamin E acts to prevent the production of peroxide lipid as a peroxide of an unsaturated fatty acid which is considered to be a material cause of the aging phenomenon, has a function of reinforcing blood vessels and activating the bloodstream, provides an anti-stress effect, and is a very important nutrient for human beings and other animals.

On the other hand, in stockbreeding, marine culturing or pet breeding, the problems of aging, reduced disease resistance, stress generation, decreased hatchability, deteriorated egg quality or meat quality, propagation disorder or mastitis, or reduction in the number of somatic cells in milk affect these animals, and a solution of these problems has hitherto been keenly demanded.

In the breeding of useful mammals including livestock animals such as cattle, pigs and horses, and pets such as dogs and cats, and experimental animals such as rats, mice and guinea pigs, reproduction is efficient because these animals are useful for human beings. As the breeding density increases, the acceleration of aging, reduced disease resistance, stress generation, accelerated oxidation of meat foods, deteriorated meat quality such as the blackening of meat foods, and propagation disorder occur more often. Propagation disorder is caused by premature birth, reduction of conception ratio, ovulatory retardation, embryo death, a weakened estrous symptom or reduced production of progesterone. Furthermore, when mastitis is generated, the number of somatic cells in milk increases and the commercial value of the milk is considerably lowered. For treating or preventing propagation disorder or mastitis, various vitamins, including vitamin E and derivatives thereof, and minerals have been conventionally added individually or in combination to the drinking water or feed and then fed to useful mammals.

Poultry such as domestic fowl, quail and turkey under overcrowded breeding conditions suffer from reduced disease resistance, stress generation, deteriorated meat quality and propagation disorder, and additionally, reduced egg quality in the case of egg layers. In order to overcome these problems, various vitamins, including vitamin E and derivatives thereof, and minerals have been conventionally added individually or in combination to the drinking water or feed and then fed to poultry.

Furthermore, in marine culturing, overcrowded breeding of marine animals causes aging problems, reduced disease resistance, stress generation, deteriorated meat quality, deteriorated egg quality and additionally, reduced hatchability and worsening body color. In order to overcome these problems, various vitamins, including vitamin E and a derivative thereof, and minerals have been conventionally added individually or in combination to the feed or premix and then fed to rainbow trout, sweet fish, carp, salmon, eel, yellow tail, globefish, flatfish, tuna, horse mackerel and prawn.

However, conventional vitamin E, a conventional derivative thereof or a combination with a mineral, when supplied to animals, cannot provide a sufficiently high effect on the treatment or prevention against aging, reduced disease resistance, stress generation, deteriorated meat quality, reduced hatchability, worsening body color, deteriorated egg quality, propagation disorder, mastitis or the generation of disease. Furthermore, vitamin E or the like is an oily substance having a high viscosity at room temperature and therefore, for example, it also has poor handleability. Under these circumstances, there has been a demand for the development of a vitamin derivative which provides, when applied to animals, a still higher effect on the treatment or prevention against aging, reduced disease resistance, stress generation, deteriorated meat quality, reduced hatchability, worsening body color, deteriorated egg quality, propagation disorder, mastitis or generation of disease, and which is easy to handle.

One problem which causes the low effects of conventional vitamin E or a conventional derivative thereof is that the natural α-tocopheryl most commonly used as a vitamin E source is expensive. The cost increases when it is used in admixture with the feed and accordingly, only a small dosage is fed to animals. Another problem is that natural α-tocopheryl or synthetic dl-α-tocopheryl has a good anti-oxidant capability but on the other hand, is itself easily oxidized. Accordingly, even if it is present in feed subjected to a heating process, it decomposes during the production or distribution process. As a result, the effect as vitamin E cannot be satisfactorily provided. Still another problem is that because α-tocopheryl and synthetic dl-α-tocopheryl or dl-α-tocopheryl acetate are oily substances having an extremely high viscosity at room temperature, they are incapable of uniform addition to feed or the like, are difficult to handle or are very cumbersome to use. Also, since they are insoluble in water, administration through the drinking water or by injection is not possible unless subjected to special processing such as emulsification. In order to overcome these problems, dl-α-tocopheryl acetate adsorbed to saccharides and formed into a powder or emulsified into a liquid product by an emulsifier is added to the feed or the like at present. The dl-α-tocopheryl acetate is relatively insusceptible to air oxidation and is stable, but has problems in that even if administered in vivo, the ester is not sufficiently converted into dl-α-tocopheryl. As a result, it fails to provide satisfactory effects as vitamin E. Also, it is difficultly absorbed into cells as compared to the dl-α-tocopheryl simple substance because it is an acetic ester compound. The dl-α-tocopheryl acetate emulsified into a liquid product by an emulsifier is bound to increase the cost because the ester is difficult to emulsify and has poor emulsification stability. Therefore, a special emulsifier is used.

A known specific example of the method of administering vitamin E to animals includes a method of supplying feed having added thereto vitamin E to egg layers to obtain eggs containing vitamin E (see, JP-B-63-50976, the term "JP-B" as used herein means an "examined Japanese patent publication").

However, the above-described conventional method for producing eggs containing vitamin E in high concentration has a problem in that the egg does not have a sufficiently high vitamin E content.

Taking into account these problems of the prior art, an object of the present invention is to provide a vitamin E source having a high absorption effect in animals, and which is easy to handle, is stable against heat and is capable of dissolving in water.

In order to achieve the above objectives, the present inventors have extensively investigated various vitamin E derivatives. As a result, they have found that dl-α-tocopheryl phosphate or a salt thereof, as one of vitamin E derivatives, is highly stable and useful because of its powder form at room temperature, provides a high vitamin E activity because it is readily absorbed into animal cells as compared with conventional dl-α-tocopheryl acetate, and can be an ideal vitamin E source due to its high biological activities available over a wide range of useful animals. Furthermore, the present inventors have verified that vitamin E is accumulated in an egg by adding α-tocopheryl phosphate or a salt thereof to the feed for egg layers.

Furthermore, the present inventors have found that a high-purity tocopheryl phosphate or a salt thereof having a tocopheryl phosphate purity of 95% or more and containing 5% or less P,P'-bistocopheryl diphosphate as an impurity has increased solubility in water in the neutral pH region as compared with tocopheryl phosphates having a low purity and can be easily administered to animals through drinking water or by injection. The present invention has been accomplished based on these findings.

SUMMARY OF THE INVENTION

Namely, the present invention provides the following.

(1) A method of supplying vitamin E to animals, which comprises administering to animals a tocopheryl phosphate, a salt thereof or a composition containing a tocopheryl phosphate or a salt thereof.

(2) The method as described in item (1), which comprises administering to animals a composition containing a tocopheryl phosphate or a salt thereof and an antioxidant.

(3) The method as described in item (1), wherein the animal is selected from the group consisting of livestock, poultry and marine animals.

(4) The method as described in item (1), wherein the tocopheryl phosphate or a salt thereof is a high-purity tocopheryl phosphate or a salt thereof comprising, as determined by a high performance liquid chromatography method, 95% or more of tocopheryl phosphate or a salt thereof and 5% or less of P,P'-bistocopheryl diphosphate or a salt thereof as impurities.

(5) The method as described in item (1), wherein the composition for administration to animals is a composition, feed or a feed additive prepared by heating at a temperature of 100° C. or higher.

(6) A method of obtaining a vitamin E-containing egg from poultry, which comprises administering feed containing a tocopheryl phosphate or a salt thereof to egg layers in breeding.

(7) The method as described in item (6), wherein the tocopheryl phosphate or a salt thereof is a high-purity tocopheryl phosphate or a salt thereof comprising, as determined by a high performance liquid chromatography method, 95% or more of tocopheryl phosphate or a salt thereof and 5% or less of P,P'-bistocopheryl diphosphate or a salt thereof as impurities.

(8) The method as described in item (6), wherein the feed is prepared by heating at a temperature of 100° C. or higher.

(9) A composition for administration to animals, which contains a high-purity tocopheryl phosphate or a salt thereof comprising, as determined by a high performance liquid chromatography method, 95% or more of tocopheryl phosphate or a salt thereof and 5% or less of P,P'-bistocopheryl diphosphate or a salt thereof as impurities.

(10) The composition as described in item (9), wherein the animal is selected from the group consisting of livestock, poultry and marine animals.

(11) The composition as described in item (9), wherein the composition for administration to animals is a composition, feed or a feed additive prepared by heating at a temperature of 100° C. or higher.

(12) A feed composition for administration to animals, which comprises a tocopheryl phosphate or a salt thereof, wherein said feed composition is prepared by heating at a temperature of 100° C. or higher.

(13) A method of quantitatively analyzing tocopheryl phosphate or a salt thereof in feed or a feed additive, which comprises using an octadecyl group-bonded polymethacrylate-base gel packed column in a high performance liquid chromatography method to quantify tocopheryl phosphate, salts thereof and P,P'-bistocopheryl diphosphates.

(14) A vitamin E source composition for administration to animals, which comprises a tocopheryl phosphate, a salt thereof, or a composition containing a tocopheryl phosphate or a salt thereof.

(15) A composition for administration to animals containing a tocopheryl phosphate or a salt thereof and an antioxidant.

(16) The composition as described in item (14) or (15), wherein the animal is selected from the group consisting of livestock, poultry and marine animals.

(17) The composition as described in item (14) or (15), wherein the tocopheryl phosphate or a salt thereof is a high-purity tocopheryl phosphate or a salt thereof comprising, as determined by a high performance liquid chromatography method, 95% or more of tocopheryl phosphate or a salt thereof and 5% or less of P,P'-bistocopheryl diphosphate or a salt thereof as impurities.

(18) The composition as described in item (14) or (15), wherein the composition for administration to animals is a composition, feed or a feed additive prepared by heating at a temperature of 100° C. or higher.

DETAILED DESCRIPTION OF THE PREFERRED EMBODIMENTS

The present invention is described in detail below.

The tocopheryl phosphate for use in the present invention is represented by formula (I), and a salt thereof is obtained by displacing the OH in the compound by ONa or OK:

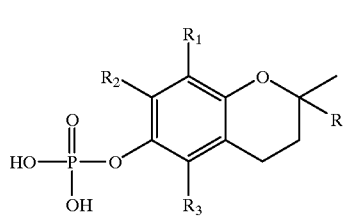
(I)

R is a long chain alkyl group represented by $C_{16}H_{33}$, for example, $-(CH_2CH_2CH_2CH(CH_3))_3-CH_3$.

With respect to the substituents $R_1$, $R_2$ and $R_3$, α-tocopheryl phosphate ($R_1$, $R_2$, $R_3$=$CH_3$), β-tocopheryl phosphate ($R_1$, $R_3$=$CH_3$, $R_2$=H), γ-tocopheryl phosphate ($R_2$, $R_3$=$CH_3$, $R_1$=H), δ-tocopheryl phosphate ($R_3$=$CH_3$, $R_1$, $R_2$=H), ζ2-tocopheryl phosphate ($R_1$, $R_2$=$CH_3$, $R_3$=H) and η-tocopheryl phosphate ($R_1$, $R_3$=$CH_3$, $R_2$=H) are known.

Among these, particularly preferred is α-tocopheryl phosphate, however, other tocopheryl esters also act as a vitamin E source and are within the scope of the present invention. Furthermore, ζ1-tocopheryl ester and ε-tocopheryl phosphate are known, and are obtained by displacing the long chain alkyl group bonded to the carbon atom adjacent to the O atom of the benzopyrane structure of the α-tocopheryl phosphate or β-tocopheryl phosphate, with a group represented by the following formula (II):

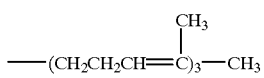
(II)

These compounds are also within the scope of the present invention. Furthermore, each tocopheryl phosphate has a d-form, an l-form and a dl-form, and all forms can be used in the present invention.

The tocopheryl phosphate represented by formula (I) can be produced by reacting a tocopherol with phosphorus oxy-trichloride and then hydrolyzing the reaction product by an acid or a base. At this time, a salt such as an alkali salt of the tocopheryl phosphate may be formed, if desired.

The addition amount of phosphorus oxytrichloride is preferably from 1 to 1.3 mol equivalents to 1 mol of tocopherol. The reaction solvent is preferably a non-reactive solvent such as benzene or toluene. The reaction temperature is from −20 to 50° C., preferably from 0 to 30° C. In order to trap the hydrogen halogenide generated during the reaction, a base such as pyridine, triethylamine, sodium carbonate or potassium carbonate may be added.

Following the above reaction, hydrolysis is performed with a base having a phosphorus-halogen bond. The base is preferably sodium hydroxide or potassium hydroxide. The aqueous solution of the base preferably has a concentration of from 1 to 3 N. The base is preferably used in an amount of from 2 to 4 mol equivalents of the tocopherol used in the reaction. The reaction may be performed using the same solvent that was employed in the reaction of tocopherol with phosphorus oxytrihalide as such. The reaction temperature is preferably from 15 to 35° C. The reaction time is preferably from 1 to 5 hours.

In this reaction, a tocopheryl phosphate represented by formula (I) and a P,P'-bistocopheryl diphosphate represented by the following formula (III) are produced simultaneously:

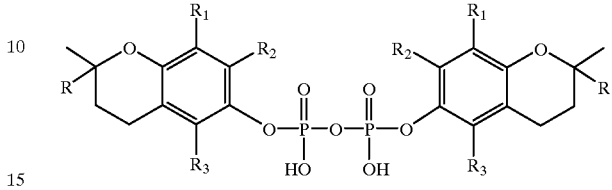
(III)

(wherein $R_1$ to $R_3$ and R have the same meanings as defined above). When these esters are dissolved in water in the neural pH region, the P,P'-bistocopheryl diphosphate represented by formula (III) is not dissolved and precipitates. When this ester of formula (III) is further subjected to a hydrolysis reaction under acidic conditions, the ester is hydrolyzed and converted into the ester of formula (I). As a result, a high-purity tocopheryl ester can be obtained.

The acid used above is preferably a sulfate or a phosphate. The acid concentration of the acidic aqueous solution is not particularly limited, however, in view of the subsequent purification process, a lower concentration is preferred. The reaction temperature and the reaction time are preferably from 70 to 110° C. and from 1 to 2 hours, respectively.

In the production of a tocopheryl phosphate represented by formula (I) by the hydrolysis of a phosphorus-halogen bond, the phosphorus-halogen bond is hydrolyzed when the hydrolysis is performed under acidic conditions. Furthermore, the —P—O—P— bond of the by-produced P,P'-bistocopheryl diphosphate represented by formula (III) can be hydrolyzed by heating.

The high-purity tocopheryl phosphate represented by formula (I) obtained according to the above-described production method has low toxicity, and the ester as such can be used as a vitamin E source. If desired, the ester may be mixed with a base in an organic solvent or a mixed solvent of water and an organic solvent to convert the same into a salt. Examples of the salt include an alkali metal salt such as a sodium salt and a potassium salt.

The tocopheryl phosphate represented by formula (I) or an alkali metal salt thereof produced as above contains little or no P,P'-bistocopheryl diphosphate and accordingly, a high purity solution can be obtained.

More specifically, when water and if desired, sodium hydroxide and phosphoric acid are added to the solution to adjust the tocopheryl phosphate concentration to 3% or less and the pH to 8.5, a high purity aqueous solution is obtained.

The method of administering the tocopheryl phosphate or a salt thereof of the present invention to animals is not particularly limited. Examples thereof include a method where the tocopheryl phosphate or a salt thereof in its original form is administered by mouth, a method where the tocopheryl phosphate or a salt thereof is added to feed, other vitamins or other medical products, and orally administered, a method where the tocopheryl phosphate or a salt thereof is applied or pasted onto the skin or mucous membrane of animals and percutaneously administered by skin absorption, and a method where the tocopheryl phosphate or a salt thereof is diluted with an appropriate solvent and after adding thereto other drugs if desired, administered by injection or infusion.

For administration to animals, the composition having blended therein the tocopheryl phosphate or a salt thereof may be formed in various shapes. Examples of the shape of the composition for administration to animals, having blended therein the tocopheryl phosphate or a salt thereof of the present invention, include feed, premix, drugs for animals, milk replacers, nutrition reinforcements, eye drops, injections, drinking water, tablets, paste, suppositories and soft capsules.

The quantitative analysis of the tocopheryl phosphate and/or a salt thereof of the present invention is described below. The quantitative analysis may be effectively performed using a long chain alkyl group-bonded polymethacrylate-base gel packed column in a high performance liquid chromatography method.

In the analysis, an eluent is fed to a liquid transfer pump, the analysis sample is injected through a sample injector into the long chain alkyl group-bonded polymethacrylate-base gel packed column for high performance chromatography to effect sample separation, and the eluate from the column is subjected to detection analysis in a detector for the ultraviolet and visible regions.

Suitable examples of the long chain alkyl group-bonded polymethacrylate-base packed column for use in the analysis of the present invention include an octadecyl group-bonded plymethacrylate-base gel packed column (for example, Shodex RS pak D18-613, DE413, manufactured by Showa Denko KK). The analysis apparatus is not particularly limited and a liquid transfer pump, sample injector, detector and recording meter typically used in high performance liquid chromatography may be employed. The column is not particularly limited with respect to construction material, shape or size. For example, a stainless steel column is preferably used. The eluent is preferably a methanol/water (including sodium acetate)-base eluent.

The tocopheryl phosphate or a salt thereof of the present invention can be quantitatively analyzed by a high performance liquid chromatography (HPLC) method using the above-described column for liquid chromatography under analysis conditions such that the column temperature is 40° C., the eluent is $MeOH/H_2O=100/1$ (containing 0.05 mol of $CH_3COONa$ in 1 liter of the eluent), the elution rate is 0.5 ml/min, the detector is a spectroscope for the ultraviolet and visible regions and the detection wavelength is 287 nm. When the tocopheryl phosphate or a salt thereof is of high purity such that the HPLC peak area of the tocopheryl phosphate or a salt thereof is 95% or more, preferably 97% or more of the entire area, and the peak area of P,P'-bistocopheryl diphosphate contained as an impurity is 5% or less, preferably 3% or less of the entire area, the solubility of the tocopheryl phosphate or a salt thereof in water having a pH of from 3 to 11 is remarkably improved.

Accordingly, in the case where the composition of the present invention is a liquid material, where the tocopheryl phosphate or a salt thereof in liquid form is dispersed or dissolved in the process of producing the composition, or where the tocopheryl phosphate or a salt thereof is mixed with a water-soluble substance, a polar substance or a substance containing a large amount of hydroxyl group to achieve uniform dispersion, the use of the high-purity tocopheryl phosphate of the present invention or a salt thereof provides a composition having improved solubility or dispersibility and in turn, is highly effective as a vitamin E source.

When the tocopheryl phosphate or a salt of the present invention is of high purity, examples of the composition as a liquid material containing the ester or a salt thereof include a nutrient reinforcing agent used in drinking water for animals, capable of achieving a stable aqueous solution at a pH of from 3 to 11, an eye drop and an injection.

When the composition of the present invention is in the form of a completely dissolved solution such as an injection, the injection is preferably adjusted to a pH of from 5 to 9. Then, a simple substance or a composite substance of two or more selected from a Na salt of tocopheryl phosphate and a K salt of tocopheryl phosphate is added. These are derivatives of salts having a higher solubility. However, when the ester or a salt thereof is added to a composition that does not need to be a completely dissolved solution, for example, a composition for use in drinking water, any salt of tocopheryl phosphate may be used as long as it is reduced in impurities and has a physiologically acceptable toxicity. A salt other than an alkali metal salt may also be used. Examples thereof include alkaline earth metal salts such as Ca, Mg and Al salts and amine salts such as hexylamine salt, however, the salt is not particularly limited.

When the composition is expected to have a sufficiently high safety and stability or solubility, the tocopheryl phosphate and a salt thereof which can be added to the composition of the present invention such as a feed, preferably has a purity and an impurity concentration as follows. The peak area of tocopheryl phosphates, as determined by the above-described high performance liquid chromatography method, is 95% or more, preferably 97% of more of the entire area and the peak area of P,P'-bistocopheryl diphosphate represented by formula (III) is 5% or less, preferably 3% or less of the entire area, although these may vary depending on the physical properties and toxicity of impurities. As a result, good solubility is obtained and uniform blending into a composition is facilitated.

Examples of the case where the high-purity tocopheryl phosphate or a salt thereof as a liquid is dispersed or dissolved in the process of producing the composition of the present invention, include spraying the tocopheryl phosphate or a salt thereof at the time of producing the composition in an extruder or pelletizing machine and forming the tocopheryl ester or a salt thereof into a liquid and then mixing with feed.

Examples of the case where the tocopheryl phosphate or a salt thereof is mixed with a water-soluble substance, a polar substance or a substance containing a large amount of a hydroxyl group to achieve uniform dispersion, include incorporating the high-purity tocopheryl phosphate into feed containing a protein or starch to produce a feed having improved dispersibility and which is highly effective as a vitamin E source. When the tocopheryl phosphate or a salt thereof is blended with feed having a high water content such as moist feed, the dispersibility is advantageously further increased.

The composition for administration to animals of the present invention can be stably blended when it is used as a feed, irrespective of the form of the feed. Examples of the feed form include powder feed, pellet feed, crumble feed, extruder feed, expansion feed, moist feed, paste feed, flow feed and liquid feed.

The tocopheryl phosphate or a salt thereof of the present invention does not lose its stability even at a high temperature of 100° C. or higher and accordingly, is most suitable for the extruder feed or expansion feed which are processed at a high temperature of 100° C. or higher. The tocopheryl phosphate or a salt thereof of the present invention is also suitable for powder feed or pellet feed which are processed through a humidification step with steam or the like.

Even when the composition containing the tocopheryl phosphate or a salt thereof is produced by a method including a heating step, the composition of the present invention can remain stable throughout the production process. The composition of the present invention may be worked using a heating or pressurizing apparatus such as a pelletizer, an expander, an extruder or other various dryers, in the heating step.

When a nutritional effect of vitamin E on animals is required, the tocopheryl phosphate or a salt thereof is usually blended in the composition of the present invention in an amount of from 0.1 to 1,000 ppm based on the entire weight of the composition. When the animal to be treated is in a growth period or in a period of stress or disease infection or infection probability, the tocopheryl phosphate or a salt thereof is blended in the feed in an amount of from 20 to 1,000 ppm. The upper limit of the blending amount may exceed the above-described range. However, in some cases, the effect accompanying an increased dose may plateau or depending on the animal, hypervitaminosis of vitamin E may result. Therefore, a dose not exceeding 1,000 ppm is preferred.

When the tocopheryl phosphate is administered in the form of an injection, a dosage range is 0.02–200 mg based on the tocopheryl phosphate per kilogram of weight of the animal.

The animals to which the composition of the present invention is administered are not particularly limited. However, the composition of the present invention is particularly effective for animals in artificial breeding or those being raised at high density. Examples of such animals include livestock, poultry and marine animals, such as domestic fowl, quail, bees, cattle, pigs, horses, dogs, cats, experimental rodent animals, rainbow trout, sweet fish, carp, salmon, eel, yellow tail, globefish, flatfish, tuna, horse mackerel and prawn. Animals in artificial breeding or those being raised at high density more readily suffer from stress than those in a normal state and accordingly, the demand for vitamin E seems to increase.

The feed or nutritional composition of the present invention is fed to livestock such as cattle, horses, pigs, goats and sheep. Propagation disorder of livestock may thereby be improved, propagation may be accelerated, mastitis may be prevented, recovery from mastitis may be accelerated or diseases such as diarrhea may be prevented.

In particular, when the feed or composition is fed to cows, due to the propagation acceleration (recovery) action, cows may enter the fertilizable state within a short time. Furthermore, mastitis can be recovered from swiftly. As a result, the amount of contaminating somatic cells in milk due to mastitis decreases, and good-quality milk having a reduced number of somatic cells can be obtained.

The effect increases when an antioxidant is added to the composition containing the tocopheryl phosphate or a salt thereof of the present invention and administered simultaneously.

Examples of the antioxidant include vitamin C and a derivative thereof, carotene and a derivative thereof, astaxanthin, lutein, dl-α-tocopheryl ester, α-tocopheryl and a derivative thereof, SOD, glutathione, catechins, and a coated product thereof. The vitamin C derivative is a single substance or a mixture of one or more substances selected from magnesium L-ascorbate, L-ascorbic acid-2-phosphoric acid and a salt thereof such as a magnesium, sodium, calcium or aluminum salt, and L-ascorbic acid-2-glucoside and a salt thereof. Examples of the carotene and a derivative thereof include P carotene, α carotene, retinoin acid, retinol, astaxanthin, canthaxanthin, zeaxanthin, lutein and an isomer thereof.

The composition of the present invention may further contain various additives. Examples of the additives include grain powder (e.g., flour, starch), bran, bean powder, saccharides (e.g., glucose), rice bran, oil cake, vitamin A, a thickener, a mineral, a seasoning, a condiment and grass.

Examples of the shape of the composition include a powder, epipastic, tablet, pellet, fine grain and capsule. The tablet or the like may be produced by a usual method using, if desired, an excipient, a disintegrator, a binder or a lubricant.

Examples of the excipient include saccharides such as lactose, D-mannitol, D-sorbitol and saccharose, starches such as corn starch and potato starch, and inorganic salts such as calcium phosphate, calcium sulfate and precipitated calcium carbonate.

Examples of the disintegrator include starches such as hydroxypropyl starch, sodium carboxymethyl starch and partial a disintegrated starches, cellulose derivatives such as calcium carboxymethyl cellulose, carboxymethyl cellulose and low substitution degree hydroxypropyl cellulose, and other synthetic polymers obtained by forming the polyvinylpyrrolidone into a cross-linked structure.

Examples of the binder include polymers such as polyvinylpyrrolidone, hydroxypropyl cellulose, hydroxypropylmethyl cellulose, gelatin and gum arabic. Examples of the lubricant include natural origin products and derivatives thereof such as talc, waxes and light silicic anhydride, and fatty acids and a metal salt thereof such as stearic aid, magnesium stearate, calcium stearate, aluminum stearate and saccharose fatty acid ester. In addition, a polymer compound such as polyethelene glycol (for example, macrogoal, trade name set forth in the $13^{th}$ Japanese Pharmacopia) may be appropriately used in the tablet.

When the composition of the present invention is used as a livestock feed, in view of handleability, facility in feeding to livestock and preference of livestock, the composition is in general preferably formed into a small grain pellet or granular product having a largest part size of from 1 to 10 mm and a smallest part size of from 1 to 10 mm. Particularly, in the case of a pellet, the composition is preferably formed into a columnar or prismatic pellet having a diameter of from 2 to 8 mm, preferably from 2 to 4 mm, and a length of from 3 to 9 mm, preferably from 4 to 7 mm. In the case of a nutritional composition other than a pellet, the shape is not particularly limited and the composition may be formed into any shape such as a spherical, ellipsoidal, cubic, parallelogram or conical form. If the size of the pellet or nutritional composition exceeds the above-described range, in adding to feed or the like and feeding to livestock, it cannot be well mixed into the feed. As a result, the intake by livestock is liable not to proceed smoothly. If the size is smaller than the above-described range, for example, in the case of a powder form, the flowability is lost and the handleability is deteriorated or feeding in a predetermined amount to livestock becomes difficult.

The composition of the present invention is preferably fed to livestock everyday or every other day continuously for from about 30 days to 3 months so as to achieve greater effects.

The livestock feed may be prepared by blending various raw materials such as the additives described above according to conventionally known preparation methods of livestock feed. For example, the livestock feed may comprise: maize: 56.2 parts (parts by weight, hereinafter the same), milo: 9.0 parts, bran: 5.0 parts, defatted rice bran: 2.3 parts, soybean cake: 7.0 parts, fish cake: 7.0 parts, alfalfa meal: 2.0 parts, calcium carbonate: 7.1 parts, calcium tertiary phosphate: 1.2 parts, salt: 0.2 part, vitamin mineral mix: 0.2 part, tallow fat: 1.0 part and corn gluten meal: 1.8 parts.

The composition of the present invention may further contain adjuvants such as a flowability improver, a consolidation inhibitor or a splash inhibitor. The composition of the present invention may be administered as it is to animals but it is usually added to the feed for animals such as livestock, poultry or marine animals in culturing or suspended in drinking water and then administered.

The animal to which the composition of the present invention is administered should be able to convert the tocopheryl phosphate or a salt thereof of the present invention into vitamin E, otherwise, satisfactory results may not be obtained. The activity of converting the tocopheryl phosphate or a salt thereof into vitamin E can be easily verified by adding a tocopheryl phosphate or a salt thereof into an extract of vital tissue such as animal blood and confirming its conversion into vitamin E. The vitamin E (tocopherol) content can be determined according to *Vitaminology Experimentation Method* (1) (K. Abe, et al., Vitamin Vol. 50, pages 453–457 (1976), compiled by Nippon Vitamin Society), using HPLC. Several tens of animals have been verified by the present inventors to have the activity of converting the tocopheryl phosphate or a salt thereof into vitamin E. Among these, animals for which the composition of the present invention is particularly useful include livestock such as cattle, pigs, horses and sheep, pets such as dogs and cats, experimental animals such as rats, mice, guinea pigs and monkeys, poultry such as broilers, layers, quail, wild duck, duck, pheasant and turkey, marine animals such as yellowtail, red sea-bream, white mouse sarranid, tilapia, globefish, tuna, flatfish, horse mackerel, saurel, salmon, carp, eel, rainbow trout, Japanese river trout, shrimps (e.g., prawn, bright prawn, spiny lobster, lobster, cray, black prawn), crabs (e.g., sea pagurian, sea crab, rhombic shell crab, rounded square shell crab), shellfish (e.g., pearl oyster, ear-shell, scallop, short-necked clam, oyster), snapping turtle, cuttlefish, octopus and sea urchin, a beetle, a hoe-shaped helmet beetle and a silkworm.

EXAMPLES

The present invention is described in greater detail below by reference to the following Examples, however, the present invention should not be construed as being limited thereto.

(1) Synthesis of Tocopheryl Phosphate

Sample I 25.0 g (0.058 mol) of dl-α-tocopherol was dissolved in 75 ml of methyl tert-butyl ether containing 9.3 g of pyridine and then cooled in an ice bath to 0° C. After cooling, 9.8 g (0.064 mol) of phosphorus oxytrichloride was added dropwise while stirring for over 5 minutes. After completing the addition, the ice bath was removed and the mixture was further reacted for 3 hours. Thereafter, 95 ml of an aqueous 2N sodium hydroxide solution was added and stirred for 10 minutes. Furthermore, 100 ml of an aqueous 10% sulfuric acid solution was added and then, the organic layer and the aqueous layer were separated using a separating funnel. The organic layer was washed with an aqueous 1N hydrochloric acid solution, dried over sodium sulfate anhydride and then concentration-dried to a solid in an evaporator. Thereto, 100 ml of toluene and 100 ml of an aqueous 1N sulfuric acid solution were added and the mixture was reacted by heating under reflux for 2 hours. The organic layer was separated and concentration-dried to a solid and 100 ml of 1-propanol was added thereto. Thereto, 25 ml of methanol having dissolved therein 2.4 g of sodium hydroxide was added dropwise and heated to from 35 to 40° C. After reacting for 1 hour, the precipitate was separated by filtration, dissolved in 1 liter of methanol and concentrated to 150 ml. Thereafter, the concentrate was added dropwise to 200 ml of acetone to deposit a white precipitate. The precipitate was washed with acetone and dried under reduced pressure to obtain 18.2 g of a white powder.

The powder thus obtained had an infrared absorption spectrum and the elemental analysis values shown below. $^{31}$P-NMR (CD$_3$OD, δ value, unit: ppm, basis: 85% phosphoric acid): 2.9

Infrared absorption spectrum (FT-IR; KBr, cm$^{-1}$): 1030 1111 1169 1250 2500–3200

Elemental analysis:

|     | Calculated (%, Note 1) | Found (%) |
| --- | --- | --- |
| C:  | 65.39 | 65.80 |
| H:  | 9.46  | 9.13  |

Note 1):
calculated for C$_{29}$H$_{50}$O$_5$PNa

The powder obtained above was then analyzed by liquid chromatography.

An analyzer was used including an octadecyl group-bonded polymethacrylate-base gel packed column (Shodex RS pak D18-613, 6φ×150 mm) and a spectral detector for the ultraviolet and visible regions, and the sample was charged into the analyzer. 10 mg of (±)-DL-tocopheryl phosphate (produced by Sigma) was dissolved in the eluent and 20 μwas charged. As a result of the analysis, a chromatogram having two large and small peaks was obtained. It was verified by $^{31}$P-NMR that the large peak was tocopheryl phosphate and the small peak was P,P-bistocopheryl diphosphate.

Eluent: MeOH/H$_2$=100/1 (containing 0.05 mol of CH$_3$COONa in 1 liter)

Elution rate: 0.5 ml/min

Spectroscope: 875-UV manufactured Nippon Bunko Sha

Detection wavelength: 287 nm

Column temperature: 40° C.

Sample II

A potassium salt of dl-α-tocopheryl phosphate was obtained in the same manner as in the synthesis of Sample I except for using potassium hydroxide in place of sodium hydroxide. The purity of the product thus obtained was almost the same as in Sample I.

Sample III and Sample IV

A calcium salt (Sample III) and a magnesium salt (Sample IV) of dl-α-tocopheryl phosphate were obtained in the same manner as in the synthesis of Sample I except for using calcium hydroxide and magnesium hydroxide, respectively.

(2) Production of Pellet 60 g of "Rucarotene 10 wt %" (produced by BASF, β-carotene content: 10 wt %), 120 g of Sample I (sodium dl-α-tocopheryl phosphate) and flour were mixed to make a total weight of 1 kg and together with the mixture thus obtained, 0.1 liter of water was fed to an extruder. This was kneaded, extruded into a bar, cut and dried to produce a pellet of vitamin E reinforcement for livestock, poultry and aquatic animals, having a diameter of 3.2 mm and a length of 5 mm (water content: 9.5%).

(3) Administration Test of Pellet to Cows 16 head of cow (Holstein, average body weight: 655 kg/head) having a somatic cell content of $4\times10^5$ cells/ml in milk and probably suffering from latent mastitis were gathered and parted into four groups each consisting of 4 head.

The pellet obtained above containing Sample I was added to feed every other day and supplied to the cows in the first group in an amount of 1 g/day.head of dl-α-tocopherol in the form of dl-α-tocopheryl phosphate. This feeding was continued for 1 month.

A pellet was prepared by the same production method having the same composition as above except for excluding only 10% of Rucarotene. The pellet thus obtained was added to feed every other day and supplied to the cows in the second group in an amount of 1 g/day.head of dl-α-tocopherol in the form of dl-α-tocopheryl phosphate. This feeding was continued for 1 month.

A pellet was prepared by the same production method having the same composition as above except for mixing dl-α-tocopheryl acetate in place of dl-α-tocopheryl phosphate. The pellet thus obtained was added to feed every other day and supplied to the cows in the third group in an amount of 1 g/day.head of vitamin E in terms of dl-α-tocopherol. This feeding was continued for 1 month.

A pellet was prepared by the same production method having the same composition as above except for mixing inorganic sodium phosphate in place of dl-α-tocopheryl phosphate. The pellet was added to feed every other day and supplied to the cows in the fourth group in an amount of 1 g/day.head of vitamin E in terms of dl-α-tocopherol. This feeding was continued for 1 month.

After 1 month, the number of somatic cells in drawn milk was measured. In the cows of the first group, the number of somatic cells in milk was reduced 1 month after administration to as low as 9% of the initial number, indicating that the administration had a great effect on the treatment of mastitis. In the cows of the second group, the number of somatic cells in milk was reduced 1 month after the administration to almost 33% of the initial number, and the administration was fairly effective but the effect in the first group was greater. In the cows of the third group, the number of somatic cells in milk was reduced 1 month after the administration to almost 71% of the initial number, but the effect was inferior to those in the first and second groups of the present invention. In the cows of the fourth group, no significant change was observed with respect to the number of somatic cells in milk.

(4) Growth Test of Rainbow Trout

A commercially available feed not containing tocopherols was used as the feed for growing a rainbow trout and thereto, calcium dl-α-tocopheryl phosphate prepared as in Sample III or magnesium dl-α-tocopheryl phosphate prepared as in Sample IV was added. The following experiment was performed to examine the effect of growth acceleration.

Experimental Method

Samples Tested

The first segment was a feed prepared by adding thereto 300 ppm of calcium dl-α-tocopheryl phosphate and 200 ppm of magnesium L-ascorbate phosphate. The second segment was a feed prepared by adding thereto 300 ppm of calcium dl-α-tocopheryl phosphate. The third segment was a feed prepared by adding thereto 300 ppm of dl-α-tocopheryl acetate.

Experimental Procedure

Yellow trout having an average body weight of 20 g/head were raised at an allocation of 525 head per one segment for 40 days.

The test results are shown in Table 1.

TABLE 1

Growth Test of Yellow Trout

|  | Daily weight increase (g/head/day) | Feed efficiency |
|---|---|---|
| First segment | 0.24 | 0.75 |
| Second segment | 0.22 | 0.72 |
| Third segment | 0.20 | 0.68 |

As seen in Table 1, the calcium salt and the magnesium salt of dl-α-tocopheryl phosphate had a growth acceleration effect on yellow trout. The feed efficiency in the table is the ratio of the increase in weight to the amount of sample added.

(5) Growth Test of Mice

Sodium dl-α-tocopheryl phosphate prepared as in Sample I was added to a feed for mice and the following experiment was performed to examine the growth acceleration effect.

Samples Tested

A feed having added thereto 10 ppm (first segment) or 100 ppm (second segment) of sodium dl-α-tocopheryl phosphate was prepared.

As a control segment, a feed having added thereto 10 ppm of dl-α-tocopheryl acetate was prepared.

Experimental Procedure

SPF mice having an average body weight of 24.5 g/head were raised at an allocation of 10 head per one segment for 29 days. The test results are shown in Table 2.

TABLE 2

Growth Test of Mouse

|  | Average increase in body weight |
|---|---|
| Control segment | 2.95 g |
| First segment | 3.80 g |
| Second segment | 4.50 g |

As seen in Table 2, sodium dl-α-tocopheryl phosphate had a growth acceleration effect on mice.

(6) Growth Test of Broiler

Potassium dl-α-tocopheryl phosphate prepared as in Sample II was added to the feed for raising broilers, and the following experiment was performed to examine the growth acceleration effect.

Experimental Method

Samples Tested

A feed having added thereto 30 ppm of potassium dl-α-tocopheryl phosphate (test segment) was prepared. The control segment was the feed free from the addition.

Experimental Procedure

Domestic fowl having an average body weight of 40 g were raised at an allocation of 20 head per one segment for 30 days. The test results are shown in Table 3.

TABLE 3

Growth Test of Broiler

|  | Test segment | Control segment |
|---|---|---|
| Average increase in body weight | 885 g | 835 g |
| Feed requirement ratio | 1.50 | 1.59 |

As seen in Table 3, dl-α-tocopheryl phosphate had a growth acceleration effect on domestic fowl. The feed requirement ratio in the table above is a ratio of the amount of feed required per unit body weight.

(7) Vitamin E Increase Test in Eggs 300 head of 204 day-year-old layers were parted into three segments each consisting of 100 head. The first segment had a continuous supply of a feed having added thereto 30 ppm of sodium dl-α-tocopheryl phosphate as in Sample I, and the second segment had a continuous supply of a feed having added thereto 30 ppm of α-tocopheryl acetate. Furthermore, the third segment as a control segment had a continuous supply of a feed for egg layers not having added thereto an α-tocopherol. Eggs laid 1 month after the administration were evaluated for vitamin E content. The results obtained are shown in the table below as a ratio to the vitamin E concentration of the control segment taken as 1.

The feed thus used had the following composition (the numerals are parts by weight):

maize: 56.3 parts, milo: 9.0 parts, bran: 5.0 parts, defatted rice bran: 2.3 parts, soybean cake: 7.0 parts, fish cake: 7.0 parts, alfalfa meal: 2.0 parts, calcium carbonate: 7.1 parts, calcium tertiary phosphate: 1.2 parts, salt: 0.2 part, vitamin-.mineral mix: 0.1 part, tallow fat: 1.0 part and corn gluten meal: 1.8 parts.

The vitamin E content in the yolk was determined according to *Vitaminology Experimentation Method* (1) (K. Abe, et al., Vitamin Vol. 50, pages 453–457 (1976), compiled by Nippon Vitamin Society) using HPLC. The value was calculated as an average of 20 eggs.

Vitamin E Accumulation Ratio in Egg

|  | Vitamin E Accumulation Ratio in Egg |
|---|---|
| First segment | 7.3 |
| Second segment | 2.5 |
| Control segment | 1.0 |

(8) Vitamin E Conversion Test

Experimental Method 2 g of intestine or viscus enucleated from the animals shown in the table below, 2 cc of blood plasma, or 2 g of solid mince was homogenized and mixed together with 5 cc of a 0.01 wt % aqueous solution of sodium dl-α-tocopheryl phosphate as Sample I under cold temperature conditions. Thereafter, the amount of dl-α-tocopherol in the solution was determined by the HPLC method. This amount was designated as the vitamin E amount before reaction. The solution obtained above was then adjusted to a pH of 4.8 with a phosphoric acid buffer and reacted with an intestine extract solution at 40° C. for 30 minutes. Thereafter, the solution was adjusted to a pH of 9 with sodium hydroxide and further reacted at 40° C. for 30 minutes, and the vitamin E was determined by the HPLC method. This was designated as the vitamin E amount after reaction. From the results thus obtained, the conversion ratio of sodium dl-α-tocopheryl phosphate into vitamin E was obtained according to the following formula for the respective animals:

$$\text{Vitamin E conversion ratio} = \frac{\text{vitamin E amount after reaction} - \text{vitamin E amount before reaction}}{\text{vitamin E amount after reaction}} \times 100$$

The results obtained are described below.

From these results, all animals were verified to have an action of converting sodium dl-α-tocopheryl phosphate into vitamin E.

Cattle intestine (75), pig intestine (90), horse plasma (63), sheep intestine (81), dog plasma (51), cat plasma (46), rad plasma (53), mouse plasma (34), guinea pig plasma (57), monkey plasma (41), domestic fowl intestine (84), quail intestine (75), wild duck intestine (86), duck intestine (72), pheasant intestine (75), turkey intestine (84), yellowtail intestine (76), red sea-bream intestine (68), white mouse sarranid intestine (88), tilapia intestine (72), globefish intestine (94), tuna intestine (84), flatfish intestine (64), horse mackerel intestine (77), saurel intestine (86), salmon intestine (79), carp intestine (72), eel intestine (82), rainbow trout intestine (73), Japanese river trout intestine (91), prawn mecentron gland (88), bright prawn mecentron gland (79), spiny lobster mecentron gland (85), lobster mecentron gland (71), cray mecentron gland (90), black prawn mecentron gland (74), sea pagurian mecentron gland (86), sea crab mecentron gland (74), rhombic shell crab mecentron gland (84), rounded square shell crab mecentron gland (84), pearl oyster solid mince (77), ear-shell solid mince (55), scallop solid mince (80), short-necked clam solid mince (68), oyster solid mince (57), snapping turtle plasma (69), cuttlefish viscus (75), octopus viscus (81), sea urchin viscus (70), beetle solid mince (79), hoe-shaped helmet beetle solid mince (72) and silkworm solid mince (66).

The numerals in the parenthesis above are values obtained according to the above formula.

The tocopheryl phosphate or a salt thereof of the present invention is readily converted into tocopherol (vitamin E) on administration to animals, and exhibits a high vitamin E activity and a large absorption effect. As a result thereof, the tocopheryl phosphate or a salt thereof of the present invention remarkably enhances the growth of livestock, poultry and marine animals and also is effective for the treatment of mastitis in cows.

The tocopheryl phosphate or a salt thereof of the present invention is stable against heat, and a composition or the like can be produced under heating. Furthermore, a high-purity tocopheryl phosphate or a salt thereof dissolves in water and is easy to handle.

While the invention has been described in detail and with reference to specific embodiments thereof, it will be apparent to one skilled in the art that various changes and modifications can be made therein without departing from the spirit and scope thereof.

What is claimed is:

1. A method comprising administering to an animal a tocopheryl phosphate or salt thereof or a composition containing a tocopheryl phosphate or a salt thereof, wherein the animal is capable of presenting symptoms of mastitis, said method further comprising ameliorating at least one of said symptoms of mastitis.

2. The method as claimed in claim 1, wherein the at least one of said symptoms that is ameliorated is the number of somatic cells in milk, said number being reduced after administration of said tocopheryl phosphate, said salt thereof or said composition.

3. A method comprising administering to an animal a tocopheryl phosphate or salt thereof or a composition containing a tocopheryl phosphate or a salt thereof,
   accelerating growth in said animal, said growth acceleration resulting from the administering of tocopheryl phosphate or said salt thereof.

4. The method as claimed in claim 3, wherein said animal is a marine animal.

5. The method as claimed in claim 4, wherein said marine animal is a trout 100° C. or higher.

6. The method as claimed in claim 3, wherein said animal is poultry.

7. A method of supplying vitamin E to egg laying poultry, said method comprising administering a feed containing tocopheryl phosphate or a salt thereof to said poultry and then collecting eggs containing vitamin E from said egg laying poultry.

8. The method as claimed in claim 7, wherein the tocopheryl phosphate or a salt thereof is a high-purity tocopheryl phosphate or a salt thereof comprising, as determined by a high performance liquid chromatography method, 95% or more of tocopheryl phosphate or a salt thereof and 5% or less of P,P'-bistocopheryl diphosphate or a salt thereof as impurities.

9. The method as claimed in claim 7, wherein the feed is prepared by heating at a temperature of 100° C. or higher.

10. A method of quantitatively analyzing tocopheryl phosphate or a salt thereof in feed or a feed additive, which comprises using an octadecyl group-bonded polymethacrylate-base gel packed column in a high performance liquid chromatography method to quantify tocopheryl phosphate, salts thereof and P,P'-bistocopheryl diphosphates.

* * * * *